(12) United States Patent
Martin

(10) Patent No.: US 6,689,810 B2
(45) Date of Patent: *Feb. 10, 2004

(54) METHOD FOR TREATING PULMONARY DISEASE STATES IN MAMMALS BY ALTERING INDIGENOUS IN VIVO LEVELS OF NITRIC OXIDE

(75) Inventor: Alain Martin, Ringoes, NJ (US)

(73) Assignee: Cellular Sciences, Inc., Flemington, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/205,353

(22) Filed: Jul. 25, 2002

(65) Prior Publication Data

US 2003/0040542 A1 Feb. 27, 2003

Related U.S. Application Data

(60) Provisional application No. 60/313,872, filed on Aug. 21, 2001.

(51) Int. Cl.[7] .......................... A61K 31/28; A61K 31/19
(52) U.S. Cl. .................... 514/492; 514/557; 514/826
(58) Field of Search .................... 514/492, 557, 514/826

(56) References Cited

U.S. PATENT DOCUMENTS

| 5,798,388 A | * | 8/1998 | Katz | 514/557 |
| 5,939,459 A | * | 8/1999 | Katz | 514/625 |
| 5,952,384 A | * | 9/1999 | Katz | 514/625 |

FOREIGN PATENT DOCUMENTS

| WO | 97/10818 | * | 3/1997 |

* cited by examiner

Primary Examiner—Kevin E. Weddington
(74) Attorney, Agent, or Firm—Richard R. Muccino

(57) ABSTRACT

The present invention pertains to a method for treating a pulmonary disease state in mammals by altering indigenous in vivo levels of nitric oxide in mammalian cells. The method comprises contacting the mammalian cells with a therapeutically effective amount of a nitric oxide mediator selected from the group consisting of pyruvates, pyruvate precursors, α-keto acids having four or more carbon atoms, precursors of α-keto acids having four or more carbon atoms, and the salts thereof. The method may further comprise contacting the mammalian cells with a therapeutic agent and a nitric oxide source selected from the group consisting of nitric oxide, nitric oxide precursors, and nitric oxide stimulators.

29 Claims, No Drawings

METHOD FOR TREATING PULMONARY DISEASE STATES IN MAMMALS BY ALTERING INDIGENOUS IN VIVO LEVELS OF NITRIC OXIDE

BACKGROUND OF THE INVENTION

This application claims priority from provisional application serial No. 60/313,872, filed Aug. 21, 2001.

FIELD OF THE INVENTION

The present invention pertains to a method for treating a pulmonary disease state in mammals by altering indigenous in vivo levels of nitric oxide in mammalian cells.

DESCRIPTION OF THE PRIOR ART

The disclosures referred to herein to illustrate the background of the invention and to provide additional detail with respect to its practice are incorporated herein by reference and, for convenience, are referenced in the following text and respectively grouped in the appended bibliography.

Nitric oxide (NO), an oxidation product of nitrogen, is produced normally by many cell types, including endothelial cells and macrophages. Nitric oxide has functions ranging from neurotransmission to vasodilatation. Nitric oxide also produces clinically useful bronchodilation (1) and is also used by the body to kill bacteria, fungal infections, viral infections, and tumors. Nitric oxide can kill these cell types because bacterial, viral, and tumor cells have no defenses against nitric oxide. Normal mammalian cells can cope with normal levels of nitric oxide by using enzyme systems to use or deactivate elevated cellular levels of nitric oxide (28–32). Nitric oxide is the main mediator of the tumoricidal action of activated macrophages (29–32). While over 30,000 papers have been written to date on nitric oxide, the role of nitric oxide in tumor biology is not completely understood. Nitric oxide appears to have both tumor promoting and inhibiting effects (31). Recent publications have implicated the reactive oxygen species made from nitric oxide during the inflammatory process as being the tumor promoting agents, not nitric oxide itself (28).

Nitric oxide has been used successfully in patients with persistent fetal circulation, persistent pulmonary hypertension in newborn (11), pulmonary hypertension secondary to cardiac dysfunction or surgery, and with adult respiratory distress syndrome (ARDS) (1,2). Nitric oxide can become a toxic oxidant when it reacts with excess oxygen radicals to produce nitrogen dioxide ($NO_2$) (1–3) and peroxynitrite (ONOO). Oxygen radicals, such as superoxide ($O_2$) and hydrogen peroxide, destroy nitric oxide and produce the toxic $NO_2$ and peroxynitrite (1–3). Peroxynitrite ion and peroxynitrous acid, formed from the interaction of nitric oxide and superoxide anions, are strong oxidant species that work against nitric oxide by inducing single-strand breaks in DNA and enhancing tumor formation and growth (28) rather than death. Superoxide and hydrogen peroxide also cause vascular constriction (1). $H_2O_2$ is the oxygen radical that appears to have the major effect on airway tone and causes contraction in both bovine and guinea pig airways.(14,15). $H_2O_2$ markedly potentiates the cytotoxic effects of eosinophil derived enzymes such as 5,8,11,14,17-eicosapentaenoic acid (16). Excess superoxide anions and hydrogen peroxide, produced during the inflammatory phase of an injury, will destroy healthy tissue surrounding the site and will mitigate the positive bronchodilation effect of nitric oxide (26). Oxygen radicals can also initiate lipid peroxidation employing arachidonic acid as an substrate producing prostaglandins and leukotrienes. $H_2O_2$ can induce arachidonic acid metabolism in alveolar macrophages (17,26). Oxygen radicals also produce 8-isoprostanes which are potent renal and pulmonary artery vasoconstrictors, bronchoconstrictors, and induce airflow obstructions (26, 27). Because oxygen radicals contribute to the instability of nitric oxide, the addition of superoxide dismutase (SOD) or catalase (15) or Vitamin E (28) protect nitric oxide to produce its desired bronchodilation (2). Hydrogen peroxide is elevated in patients with chronic obstructive pulmonary disease (COPD), asthma, and ARDS (26). A study in 28 patients showed a significant correlation between oxygen radical generation in white blood cell count (WBC) and the degree of bronchial hyperreactivity in vivo in nonallergic patient's (18). The authors suggested that direct suppression of oxygen radical production by corticosteriods might be involved.

Nitrogen dioxide is a major air pollutant and a deep lung irritant. Nitrogen dioxide is formed in combustion processes, either directly or through secondary oxidation of nitric oxide (8). Nitrogen dioxide causes pulmonary inflammation, lower levels of lung antioxidants (10), deterioration of respiratory defense mechanisms, and increases susceptibility to respiratory pathogens (8). Nitrogen dioxide can also increase the incidence and severity of respiratory infections, can reduce lung function, and can aggravate the symptoms of asthmatics or subjects with COPD (8). Nitric oxide can also combine with superoxide anions to form peroxynitrite, which can generate the highly reactive hydroxyl anion (OH). According to epidemiological studies, the population group most susceptible to these adverse effects is small children, either with and without asthma (8). This group develops respiratory illnesses, shortness of breath, persistent wheeze, chronic cough, chronic phlegm, and bronchitis (4–8). Even though asthmatic children have increased amounts of exhaled nitric oxide over non-asthmatic children, there is persuasive evidence that higher levels of nitric oxide are decreased by the overproduction of oxygen radicals during the inflammatory process (1–8). This becomes a problematic situation for which the only solution is denied by the circumstance inherent in the problem. The underlying chronic inflammatory process in asthma, which induces nitric oxide synthesis, also produces excess oxygen radicals, which will destroy nitric oxide (6). The inhalation of a pulmonary irritant has been shown to enhance nitric oxide production by alveolar macrophages in rats, which also produces an increased level of oxygen radical that can react directly with nitric oxide to produce $NO_2$ (1–3, 6).

Sodium pyruvate is an antioxidant that reacts directly with oxygen radicals to neutralize them. In macrophages, and other cell lines, sodium pyruvate regulates the production and level of inflammatory mediators including oxygen radical production and also increases the synthesis of nitric oxide (9). It can specifically lower the overproduction of superoxide anions. Sodium pyruvate also increases cellular levels of glutathione, a major cellular antioxidant (12). It was recently discovered that glutathione is reduced dramatically in antigen-induced asthmatic patients (13) and inhaled glutathione does not readily enter cells. Pyruvate does enter all cells via a transport system and can also cross the blood brain barrier. Excess sodium pyruvate beyond that needed to neutralize oxygen radicals will enter the bronchial and lung cells. All cells have a transport system that allow cells to concentrate pyruvate at higher concentrations than serum levels. In the cell, pyruvate raises the pH level, increases levels of ATP, decreasing levels of ADP and cAMP, and increases levels of GTP, while decreasing levels of cGMP.

Nitric oxide acts in the opposite mode by increasing levels of cGMP and ADP, and requires an acid pH range in which to work (19).

U.S. Pat. No. 6,063,407 (Zapol et al.) discloses methods of treating, inhibiting or preventing vascular thrombosis or arterial restenosis in a mammal. The methods include causing the mammal to inhale a therapeutically effective concentration of gaseous nitric oxide. Also disclosed are methods that include the administration of the following types of agents in conjunction with inhaled nitric oxide: compounds that potentiate the beneficial effects of inhaled nitric oxide, and antithrombotic agents that complement or supplement the beneficial effects of inhaled nitric oxide.

U.S. Pat. No. 6,020,308 (Dewhirst et al.) discloses the use of an inhibitor of NO activity, such as a nitric oxide scavenger or an NO synthase inhibitor, as an adjunct to treatment of inappropriate tissue vascularization disorders U.S. Pat. No. 5,891,459 (Cooke et al.) discloses the maintenance or improvement of vascular function and structure by long term administration of physiologically acceptable compounds, such as L-arginine, L-lysine, physiologically acceptable salts thereof, and polypeptide precursors thereof, which enhance the level of endogenous nitric oxide or other intermediates in the NO induced relaxation pathway in the host. In or in combination, other compounds, such as B6, folate, B12, or an antioxidant, which provide for short term enhancement of nitric oxide, either directly or by physiological processes may be employed.

U.S. Pat. No. 5,873,359 (Zapol et al.) discloses a method for treating or preventing bronchoconstriction or reversible pulmonary vasoconstriction in a mammal, which method includes causing the mammal to inhale a therapeutically effective concentration of gaseous nitric oxide or a therapeutically effective amount of a nitric oxide releasing compound, and an inhaler device containing nitric oxide gas and/or a nitric oxide releasing compound.

U.S. Pat. No. 5,767,160 (Kaesemeyer) discloses a therapeutic in vitro or in vivo mixture comprising L-arginine and an agonist of nitric oxide synthase, such as nitroglycerin for the treatment of diseases related to vasoconstriction. The vasoconstriction is relieved by stimulating the constitutive form of nitric oxide synthase (cNOS) to produce native nitric oxide. The native NO has superior beneficial effect when compared to exogenous NO produced by a L-arginine independent pathway in terms of the ability to reduce clinical endpoints and mortality.

U.S. Pat. No. 5,543,430 (Kaesemeyer) discloses a therapeutic mixture comprising a mixture of L-arginine and an agonist of nitric oxide synthase such as nitroglycerin for the treatment of diseases related to vasoconstriction. The vasoconstriction is relieved by stimulating the constitutive form of nitric oxide synthase to produce native nitric oxide. The native NO has superior beneficial effect when compared to exogenous NO produced by a L-arginine independent pathway in terms of the ability to reduce clinical endpoints and mortality.

U.S. Pat. No. 5,428,070 (Cooke et al.) discloses a method for treating atherogenesis and restenosis by long term administration of physiologically acceptable compounds which enhance the level of endogenous nitric oxide in the host. Alternatively, or in combination, other compounds may be administered which provide for short term enhancement of nitric oxide, either directly or by physiological processes. In addition, cells may be genetically engineered to provide a component in the synthetic pathway to nitric oxide, so as drive the process to enhance nitric oxide concentration, particularly in conjunction with the administration of a nitric oxide precursor.

U.S. Pat. No. 5,286,739 (Kilbourn et al.) discloses an anti-hypotensive formulation comprising an essentially arginine free or low arginine (less than about 0.1%, most preferably, about 0.01%) containing a mixture of amino acids. The formulation may include ornithine, citrulline, or both. A method for prophylaxis and treatment of systemic hypotension in an animal is also provided. A method for treating hypotension caused by nitric oxide synthesis through administering a low or essentially arginine free parenteral formulation to an animal, so as to reduce or eliminate nitric oxide synthesis is described. A method for treating an animal in septic shock is also disclosed, comprising administering to the animal an anti-hypotensive formulation comprising a mixture of amino acids, which is essentially arginine free. Prophylaxis or treatment of systemic hypotension, particularly that hypotension incident to chemotherapeutic treatment with biologic response modifiers, such as tumor necrosis factor or interleukin-1 or 2, may be accomplished through the administration of the defined anti-hypotensive formulations until physiologically acceptable systolic blood pressure levels are achieved in the animal. Treatment of an animal for septic shock induced by endotoxin may also be accomplished by administering to the animal the arginine free formulations described.

U.S. Pat. No. 5,217,997 (Levere et al.) discloses a method for treating a high vascular resistance disorder in a mammal by administering to a mammalian organism in need of such treatment a sufficient amount of L-arginine or pharmaceutically acceptable salt thereof to treat a high vascular resistance disorder. The L-arginine is typically administered in the range of about 1 mg to 1500 mg per day. High vascular resistance disorders include hypertension, primary or secondary vasospasm, angina pectoris, cerebral ischemia and preeclampsia. Also disclosed is a method for preventing or treating bronchial asthma in a mammal by administering to a mammalian organism in need of such prevention or treatment a sufficient amount of L-arginine to prevent or treat bronchial asthma.

U.S. Pat. No. 5,158,883 (Griffith) discloses pharmaceutically pure physiologically active NG-aminoarginine (i.e., the L or D, L form), or pharmaceutically acceptable salts thereof, administered in a nitric oxide synthesis inhibiting amount to a subject in need of such inhibition (e.g., a subject with low blood pressure or needing immunosuppressive effect) or added to a medium containing isolated organs, intact cells, cell homogenates or tissue homogenates in an amount sufficient to inhibit nitric oxide formation to elucide or control the biosynthesis, metabolism or physiological role of nitric oxide. The NG-amino-L-arginine is prepared and isolated as a pharmaceutically pure compound by reducing NG-nitro-L-arginine, converting L-arginine by-product to L-ornithine with arginase and separating NG-amino-L-arginine from the L-ornithine. NG-amino-D,L-arginine is prepared in similar fashion starting with NG-nitro-D,L-arginine.

U.S. Pat. Nos. 5,798,388, 5,939,459, and 5,952,384 (Katz) pertain to a method for treating various disease states in mammals caused by mammalian cells involved in the inflammatory response and compositions useful in the method. The method comprises contacting the mammalian cells participating in the inflammatory response with an inflammatory mediator. The inflammatory mediator is present in an amount capable of reducing the undesired inflammatory response and is an antioxidant. The preferred inflammatory mediator is a pyruvate. Katz discloses the treatment of airway diseases of the lungs such as bronchial asthma, acute bronchitis, emphysema, chronic obstructive emphysema, centrilobular emphysema, panacinar emphysema, chronic obstructive bronchitis, reactive airway disease, cystic fibrosis, bronchiectasis, acquired bronchiectasis, kartaagener's syndrone; atelectasis, acute atelectasis, chronic atelectasis, pneumonia, essential thrombocytopenia, legionnaires disease, psittacosis, fibrogenic dust disease, diseases due to organic dust, diseases due to irritant gases and chemicals, hypersensitivity diseases of the lung, idiopathic infiltrative diseases of the lungs and the like by inhaling pyruvate containing compositions. The pyruvate acts as an inflammatory response mediator and reduces the undesired inflammatory response in mammalian cells.

U.S. Pat. No. 5,296,370 (Martin et al.) discloses therapeutic compositions for preventing and reducing injury to mammalian cells and increasing the resuscitation rate of injured mammalian cells. The therapeutic composition comprises (a) pyruvate selected from the group consisting of pyruvic acid, pharmaceutically acceptable salts of pyruvic acid, and mixtures thereof, (b) an antioxidant, and (c) a mixture of saturated and unsaturated fatty acids wherein the fatty acids are those fatty acids required for the resuscitation of injured mammalian cells.

While the above therapeutic compositions and methods are reported to inhibit the production of reactive oxygen intermediates, none of the disclosures describe methods for treating a pulmonary disease state in mammals by altering indigenous in vivo levels of nitric oxide in mammalian cells.

SUMMARY OF THE INVENTION

The present invention pertains to a method for treating a pulmonary disease state in mammals by altering indigenous in vivo levels of nitric oxide in mammalian cells. The method comprises contacting the mammalian cells with a therapeutically effective amount of a nitric oxide mediator selected from the group consisting of pyruvates, pyruvate precursors, α-keto acids having four or more carbon atoms, precursors of α-keto acids having four or more carbon atoms, and the salts thereof.

The method may further comprise contacting the mammalian cells with a nitric oxide source selected from the group consisting of nitric oxide, nitric oxide precursors, and nitric oxide stimulators. The method still may further comprise contacting the mammalian cells with a therapeutic agent such as antibacterials, antivirals, antifungals, antihistamines, proteins, enzymes, hormones, nonsteroidal anti-inflammatories, cytokines, or steroids. The method may still further comprise contacting the mammalian cells with both a nitric oxide source and a therapeutic agent.

DETAILED DESCRIPTION OF THE INVENTION

In accord with the present invention, a method is provided for treating a pulmonary disease state in mammals by altering indigenous in vivo levels of nitric oxide in mammalian cells. The method comprises contacting the mammalian cells, preferably white blood cells, with a therapeutically effective amount of a nitric oxide mediator. The nitric oxide mediator may be selected from the group consisting of pyruvates, pyruvate precursors, α-keto acids having four or more carbon atoms, precursors of α-keto acids having four or more carbon atoms, and the salts thereof.

Nitric oxide is known to kill bacteria, viruses, funguses, and tumors, however, nitric oxide can be damaged by oxygen radicals and thus will not be effective. Nitric oxide mediators such as pyruvates and α-keto acids can protect nitric oxide from oxygen radicals and permit nitric oxide to better treat bacterial infections, viral infections, fungal infections, and tumors. The pulmonary tumors suitable for treatment include epidermoid (squamous cell) carcinoma, small cell (oat cell) carcinoma, adenocarcinoma, and large cell (anaplastic) carcinoma. Nitric oxide mediators can protect naturally produced nitric oxide as well as nitric oxide co-administered with the nitric oxide mediator. The nitric oxide mediator may be administered prior to administration of the nitric oxide source, concomitantly with administration of nitric oxide source, or administered after administration of nitric oxide source. Nitric oxide is generally administered as a gas and so will be very effective in the lungs and sinuses. In many cases, pulmonary diseases produce infections that this nitric oxide mediator/nitric oxide combination can treat. The nitric oxide mediator may be inhaled first to eliminate hydrogen peroxide followed by inhalation of nitric oxide which would not then be destroyed by hydrogen peroxide. The nitric oxide mediator/nitric oxide combination would be especially effective for treating pulmonary diseases such as bronchial asthma, acute bronchitis, emphysema, chronic obstructive emphysema, centrilobular emphysema, panacinar emphysema, chronic obstructive bronchitis, reactive airway disease, cystic fibrosis, bronchiectasis, acquired bronchiectasis, kartaagener's syndrome, acelectasis, acute atelectasis, chronic acelectasis, pneumonia, essential thrombocytemia, legionnaire's disease, psittacosis, fibrogenic dust disease, diseases due to organic dust, diseases due to irritant gases and chemicals, hypersensitivity diseases of the lung, and idiopathic infiltrative diseases of the lungs.

The nitric oxide mediator of the present invention may be any mediator that will protect nitric oxide and thereby help treat a disease state in mammals by altering indigenous in vivo levels of nitric oxide in mammalian cells. Preferably, the nitric oxide mediator is selected from the group consisting of pyruvates, pyruvate precursors, α-keto acids having four or more carbon atoms, precursors of α-keto acids having four or more carbon atoms, and the salts thereof. The pyruvates may be selected from the group consisting of pyruvic acid, lithium pyruvate, sodium pyruvate, potassium pyruvate, magnesium pyruvate, calcium pyruvate, zinc pyruvate, manganese pyruvate, and mixtures thereof. The pyruvate precursors may be selected from the group consisting of pyruvyl-glycine, pyruvyl-alanine, pyruvyl-leucine, pyruvyl-valine, pyruvyl-isoleucine, pyruvyl-phenylalanine, pyruvamide, salts of pyruvic acid, and mixtures thereof. The α-keto acids having four or more carbon atoms may be selected from the group consisting of oxaloacetic acid, keto-glutaric acid, keto-butyric acid, keto-adipic acid, keto-caproic acid, keto-isovaleric acid, their salts and mixtures thereof. The precursors of α-keto acids having four or more carbon atoms may be selected from the group consisting of α-keto acid-glycine, α-keto acid-cystine, α-keto acid-alanine, α-keto acid-leucine, α-keto acid-valine, α-keto acid-isoleucine, α-keto acid-phenylalanine, α-keto amide, their salts and mixtures thereof.

Preferred salts of the nitric oxide mediator are salts that do not produce an adverse effect on the mammalian cell when applied as a salt of the nitric oxide mediator. Typical salts would be the lithium, sodium, potassium, aluminum, magnesium, calcium, zinc, manganese, ammonium, and the like, and mixtures thereof.

The term "precursors", as used herein refers to compounds which undergo biotransformation prior to exhibiting their pharmacological effects. The chemical modification of drugs to overcome pharmaceutical problems has also been termed "drug latentiation." Drug latentiation is the chemical modification of a biologically active compound to form a new compound which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms precursors, prodrugs, latentiated drugs, and bioreversible derivatives are used interchangeably. By inference, latentiation implies a time lag element or time component involved in regenerating the bioactive parent molecule in vivo. The term precursor is general in that it includes latentiated drug derivatives as well as those substances which are converted after administration to the actual substance which combines with receptors. The term precursor is a generic term for agents which undergo biotransformation prior to exhibiting their pharmacological actions.

The pulmonary disease states for which nitric oxide mediator treatment may be employed may be selected from the group consisting of bacterial infections, fungal infections, viral infections, and tumors. The tumors may be selected from the group consisting of epidermoid carcinomas, small cell carcinomas, adenocarcinomas, and large cell carcinomas. Preferably, the disease state is selected from the group consisting of bacterial infections, fungal infections, and viral infections.

In one embodiment, the levels of nitric oxide in the mammalian cells are abnormally low in the disease state. In another embodiment, the levels of nitric oxide in the mammalian cells are abnormally high in the disease state. Whether the levels of nitric oxide are abnormally low or abnormally high can be determined from the level of nitric oxide a patient exhales. Knowing what a patient exhales determines the dose of nitric oxide the patient receives. Normal lung levels of nitric oxide are 2–10 ppb. In the sinus area, the levels of nitric oxide are 1000× that ranging form 1–30 ppm. Macrophages produce 100–500 ppb to kill bacteria. People with normal levels of nitric oxide exhale 2–5 ppb. Asthmatics exhale 5–100 times that level, i.e. 100–300 ppb. Patients with ARDs are treated with 10–30 ppm. Excess nitric oxide in excess of 50 ppm will react with $H_2O_2$ to produce $NO_2$ which is toxic. Nitric oxide does not produce cancer. The normal volume of nitric oxide used is 20 ppm times 30 minutes.

The amount of nitric oxide mediator present in the therapeutic compositions of the present invention is a therapeutically effective amount. A therapeutically effective amount of nitric oxide mediator is that amount of nitric oxide mediator necessary to protect both naturally produced nitric oxide as well as nitric oxide co-administered with the nitric oxide mediator thereby permitting nitric oxide to better treat bacterial infections, viral infections, fungal infections, and tumors. The exact amount of nitric oxide mediator is a matter of preference subject to such factors as the type of condition being treated as well as the other ingredients in the composition. In a preferred embodiment, the nitric oxide mediator is administered from about 0.0001 to about 0.05 millimoles per dose, preferably about 0.0005 to about 0.03 millimole per dose, more preferably about 0.0005 to about 0.01 millimoles per dose, still more preferably about 0.0005 to about 0.005 millimoles per dose, still more preferably about 0.0005 to about 0.0035, and most preferably about 0.001 to about 0.003 millimoles per dose. A 5 ml solution of 0.5 millimole concentration nitric oxide mediator will contain 0.0025 millimoles of nitric oxide mediator. The optimal dosage of nitric oxide, nitric oxide precursor, or nitric oxide stimulator for any given patient, can readily be determined and will depend on factors such as the type and severity of the disease condition being treated.

In a preferred embodiment, the method may further comprise contacting the mammalian cells with a nitric oxide source selected from the group consisting of nitric oxide, nitric oxide precursors, and nitric oxide stimulators. Preferably, the nitric oxide source is nitric oxide. Preferably, the nitric oxide precursor or nitric oxide stimulator is selected from the group consisting of L-arginine, ADP, and arachidonic acid. More preferably, the nitric oxide precursor or nitric oxide stimulator is L-arginine.

The term "nitric oxide source" includes nitric oxide, nitric oxide precursors, and nitric oxide stimulators. Nitric oxide (mononitrogen monoxide, nitrogen monoxide, NO) has a molecular weight of 30.01. Nitric oxide is a colorless gas, bums only when heated with hydrogen, is deep blue when liquid, and bluish-white when solid. The melting point of nitric oxide is −163.6° C. and the boiling point is −151.7° C. Nitric oxide contains an odd number of electrons and is paramagnetic. The solubility of nitric oxide in water (ml/100 ml; 1 atm) is: 4.6 (20° C.); 2.37 (60° C.). A nitric oxide precursor is a substance from which nitric oxide is formed and in this text also includes salts.

The pulmonary disease states for which nitric oxide mediator/nitric oxide source treatment may be employed may be selected from the group consisting of bacterial infections, fungal infections, viral infections, and tumors. The tumors may be selected from the group consisting of epidermoid carcinomas, small cell carcinomas, adenocarcinomas, and large cell carcinomas. Preferably, the disease state is selected from the group consisting of bacterial infections, fungal infections, and viral infections.

Other pulmonary disease states for which nitric oxide mediator/nitric oxide source treatment may be employed may be selected from the group consisting of bronchial asthma, acute bronchitis, emphysema, chronic obstructive emphysema, centrilobular emphysema, panacinar emphysema, chronic obstructive bronchitis, reactive airway disease, cystic fibrosis, bronchiectasis, acquired bronchiectasis, kartaagener's syndrone, acelectasis, acute atelectasis, chronic acelectasis, pneumonia, essential thrombocytemia, legionnaire's disease, psittacosis, fibrogenic dust disease, diseases due to organic dust, diseases due to irritant gases and chemicals, hypersensitivity diseases of the lung, idiopathic infiltrative diseases of the lungs, chronic obstructive pulmonary disorder, and adult respiratory distress syndrome. Preferred disease states are emphysema and asthma.

The amount of nitric oxide source present in the therapeutic compositions of the present invention is a therapeutically effective amount. A therapeutically effective amount of nitric oxide source is that amount of nitric oxide source necessary to treat bacterial infections, viral infections, fungal infections, and tumors. The exact amount of nitric oxide source is a matter of preference subject to such factors as the type of condition being treated as well as the other ingredients in the composition. In a preferred embodiment, nitric oxide source is present in the therapeutic composition in an amount from about 10 ppm to about 50 ppm, preferably from about 15 ppm to about 45 ppm, more preferably from about 20 ppm to about 40 ppm, and most preferably from about 25 ppm to about 35 ppm, by weight of the therapeutic composition. Preferably, the nitric oxide source is administered over a 7 hour exposure by inhalation.

The nitric oxide mediator may be administered prior to administration of the nitric oxide source, concomitantly with administration of nitric oxide source, or administered after administration of nitric oxide source.

In another preferred embodiment, the method may further comprise contacting the mammalian cells with a therapeutic agent. The therapeutic agent may be selected from the group consisting of antibacterials, antivirals, antifungals, antitumors, antihistamines, proteins, enzymes, hormones, nonsteroidal anti-inflammatories, cytokines, and steroids. The therapeutic agent may be administered prior to administration of the nitric oxide mediator, concomitantly with administration of the nitric oxide mediator, or after administration of the nitric oxide mediator.

The amount of therapeutic agent present in the therapeutic compositions of the present invention is a therapeutically effective amount. A therapeutically effective amount of a therapeutic agent is the usual amount of therapeutic agent necessary to treat the particular condition. The exact amount of therapeutic agent is a matter of preference subject to such factors as the type of condition being treated as well as the other ingredients in the composition. In general, the amount of antibacterial agent present is the ordinary dosage required to obtain the desired result. Such dosages are known to the skilled practitioner in the medical arts and are not a part of the present invention. The therapeutic agent may be administered prior to administration of the nitric oxide mediator, concomitantly with administration of nitric oxide mediator, or administered after administration of nitric oxide mediator.

The antibacterial agents which may be employed in the therapeutic compositions may be selected from a wide variety of water-soluble and water-insoluble drugs, and their acid addition or metallic salts, useful for treating pulmonary diseases. Both organic and inorganic salts may be used provided the antibacterial agent maintains its medicament value. The antibacterial agents may be selected from a wide range of therapeutic agents and mixtures of therapeutic agents which may be administered in sustained release or prolonged action form. Nonlimiting illustrative specific examples of antibacterial agents include bismuth containing compounds, sulfonamides; nitrofurans, metronidazole, tinidazole, nimorazole, benzoic acid; aminoglycosides, macrolides, penicillins, polypeptides, tetracyclines, cephalosporins, chloramphenicol, and clidamycin. Preferably, the antibacterial agent is selected from the group consisting of bismuth containing compounds, such as, without limitation, bismuth aluminate, bismuth subcitrate, bismuth subgalate, bismuth subsalicylate, and mixtures thereof; the sulfonamides; the nitrofurans, such as nitrofurazone, nitrofurantoin, and furozolidone; and miscellaneous antibacterials such as metronidazole, tinidazole, nimorazole, and benzoic acid; and antibiotics, including the aminoglycosides, such as gentamycin, neomycin, kanamycin, and streptomycin; the macrolides, such as erythromycin, clindamycin, and rifamycin; the penicillins, such as penicillin G, penicillin V, Ampicillin and amoxicillin; the polypeptides, such as bacitracin and polymyxin; the tetracyclines, such as tetracycline, chlorotetracycline, oxytetracycline, and doxycycline; the cephalosporins, such as cephalexin and cephalothin; and miscellaneous antibiotics, such as chloramphenicol, and clidamycin. More preferably, the antibacterial agent is selected from the group consisting of bismuth aluminate, bismuth subcitrate, bismuth subgalate, bismuth subsalicylate, sulfonamides, nitrofurazone, nitrofurantoin, furozolidone, metronidazole, tinidazole, nimorazole, benzoic acid, gentamycin, neomycin, kanamycin, streptomycin, erythromycin, clindamycin, rifamycin, penicillin G, penicillin V, Ampicillin amoxicillin, bacitracin, polymyxin, tetracycline, chlorotetracycline, oxytetracycline, doxycycline, cephalexin, cephalothin, chloramphenicol, and clidamycin.

The amount of antibacterial agent which may be employed in the therapeutic compositions of the present invention may vary depending upon the therapeutic dosage recommended or permitted for the particular antibacterial agent. In general, the amount of antibacterial agent present is the ordinary dosage required to obtain the desired result. Such dosages are known to the skilled practitioner in the medical arts and are not a part of the present invention. In a preferred embodiment, the antibacterial agent in the therapeutic composition is present in an amount from about 0.01% to about 10%, preferably from about 0.1% to about 5%, and more preferably from about 1% to about 3%, by weight.

The antiviral agents which may be employed in the therapeutic compositions may be selected from a wide variety of water-soluble and water-insoluble drugs, and their acid addition or metallic salts, useful for treating pulmonary diseases. Both organic and inorganic salts may be used provided the antiviral agent maintains its medicament value. The antiviral agents may be selected from a wide range of therapeutic agents and mixtures of therapeutic agents which may be administered in sustained release or prolonged action form. Nonlimiting illustrative categories of such antiviral agents include RNA synthesis inhibitors, protein synthesis inhibitors, immunostimulating agents, protease inhibitors, and cytokines. Nonlimiting illustrative specific examples of such antiviral agents include the following medicaments.

(a) Acyclovir (9-[(2-hydroxyethyloxy)methyl]guanine, trade name—ZOVIRAX™) is an antiviral drug for oral administration. Acyclovir is a white, crystalline powder with a molecular weight of 225 daltons and a maximum solubility in water of 2.5 mg/mL at 37° C. Acyclovir is a synthetic purine nucleoside analogue with in vitro and in vivo inhibitory activity against human herpes viruses including herpes simplex types 1 (HSV-1) and 2 (HSV-2), varicella-zoster virus (VZV), Epstein-Barr virus (EBV), and cytomegalovirus (CMV).

(b) Foscarnet sodium (phosphonoformic acid trisodium salt, trade name—FOSCAVIR™) is an antiviral drug for intravenous administration. Foscarnet sodium is a white, crystalline powder containing 6 equivalents of water of hydration with an empirical formula of $Na_3CO_6P.6\ H_2O$ and a molecular weight of 300.1. Foscarnet sodium has the potential to chelate divalent metal ions such as calcium and magnesium, to form stable coordination compounds. Foscarnet sodium is an organic analogue of inorganic pyrophosphate that inhibits replication of all known herpes viruses in vitro including cytomegalovirus (CMV), herpes simplex virus types 1 and 2 (HSV-1, HSV-2), human herpes virus 6 (HHV-6), Epstein-Barr virus (EBV), and varicella-zoster virus (VZV). Foscarnet sodium exerts its antiviral activity by a selective inhibition at the pyrophosphnte binding site on virus-specific DNA polymerases and reverse transcriptases at concentrations that do not affect cellular DNA polymerases.

(c) Ribavirin (1-beta-D-ribofuranosyl-1,2,4-triazole-3-carboxamide, trade name—VIRAZOLE™) is an antiviral drug provided as a sterile, lyophilized powder to be reconstituted for aerosol administration. Ribavirin is a synthetic nucleoside which is a stable, white, crystalline compound with a maximum solubility in water of 142 mg/ml at 25° C. and with only a slight solubility in ethanol. The empirical formula is $C_8H_{12}N_4O_5$ and the molecular weight is 244.2 Daltons. Ribavirin has antiviral inhibitory activity in vitro against respiratory syncytial virus, influenza virus, and herpes simplex virus. Ribavirin is also active against respiratory syncytial virus (RSV) in experimentally infected cotton rats. In cell cultures, the inhibitory activity of ribavirin for RSV is selective. The mechanism of action is unknown. Reversal of the in vitro antiviral activity by guanosine or xanthosine suggests ribavirin may act as an analogue of these cellular metabolites.

(d) Vidarabine (adenine arabinoside, Ara-A, 9-βD-arabinofuranosyladenine monohydrate, trade name—VIRA-A™) is an antiviral drug. Vidarabine is a purine nucleoside obtained from fermentation cultures of Streptomyces antibioticus. Vidarabine is a white, crystalline solid with the empirical formula, $C_{10}H_{13}N_5O_4.H_2O$. The molecular weight of vidarabine is 285.2, the solubility is 0.45 mg/ml at 25° C., and the melting point ranges from 260° to 270° C. Vidarabine possesses in vitro and in vivo antiviral activity against Herpes simplex virus types 1 and 2 (HSV-1 and HSV-2), and in vitro activity against varicella-zoster virus (VZV). The antiviral mechanism of action has not yet been established. Vidarabine is converted into nucleotides which inhibit viral DNA polymerase.

(e) Ganciclovir sodium (9-(1,3-dihydroxy-2-propoxymethyl)guanine, monosodium salt, trade name—CYTOVENE™) is an antiviral drug active against cytomegalovirus for intravenous administration. Ganciclovir sodium has a molecular formula of $C_9H_{12}N_6NaO_4$ and a molecular weight of 277.21. Ganciclovir sodium is a white lyophilized powder with an aqueous solubility of greater than 50 mg/mL at 25° C. Ganciclovir is a synthetic nucleoside analogue of 2'-deoxyguanosine that inhibits replication of herpes viruses both in vitro and in vivo. Sensitive human viruses include cytomegalovirus (CMV), herpes simplex virus-1 and -2 (HSV-1, HSV-2), Epstein-Barr virus (EBV), and varicella zoster virus (VZV).

(f) Zidovudine [azidothymidine (AZT), 3'-azido-3'-deoxythymidine, trade name—RETROVIR™] is an antiretroviral drug active against human immunodeficiency virus (HIV) for oral administration. Zidovudine is a white to beige, odorless, crystalline solid with a molecular weight of 267.24 daltons and a molecular formula of $C_{10}H_{13}N_5O_4$. Zidovudine is an inhibitor of the in vitro replication of some retroviruses including HIV (also known as HTLV III, LAV, or ARV). Zidovudine is a thymidine analogue in which the 3'hydroxy (—OH) group is replaced by an azido (—N3) group.

(g) Phenol (carbolic acid) is a topical antiviral, anesthetic, antiseptic, and antipruritic drug. Phenol is a colorless or white crystalline mass which is soluble in water, has a characteristic odor, a molecular formula of $C_6H_6O$, and a molecular weight of 94.11.

(h) Amantadine hydrochloride (1-adamantanamine hydrochloride, trade name—SYMMETREL™) has pharmacological actions as both an anti-Parkinson and an antiviral drug. Amantadine hydrochloride is a stable white or nearly, white crystalline powder, freely soluble in water and soluble in alcohol and in chloroform. The antiviral activity of amantadine hydrochloride against influenza A is not completely understood but the mode of action appears to be the prevention of the release of infectious viral nucleic acid into the host cell.

(i) Interferon alfa-n3 (human leukocyte derived, trade name—ALFERON™) is a sterile aqueous formulation of purified, natural, human interferon alpha proteins for use by injection. Interferon alfa-n3 injection consists of interferon alpha proteins comprising approximately 166 amino acids ranging in molecular weights from 16,000 to 27,000 daltons. Interferons are naturally occurring proteins with both antiviral and antiproliferative properties.

Preferred antiviral agents to be employed may be selected from the group consisting of acyclovir, foscarnet sodium, ribavirin, vidarabine, ganciclovir sodium, zidovudine, phenol, amantadine hydrochloride, and interferon alfa-n3. In a preferred embodiment, the antiviral agent is selected from the group consisting of acyclovir, foscarnet sodium, ribavirin, vidarabine, and ganciclovir sodium. In a more preferred embodiment, the antiviral agent is acyclovir.

The amount of antiviral agent which may be employed in the therapeutic compositions of the present invention may vary depending upon the therapeutic dosage recommended or permitted for the particular antiviral agent. In general, the amount of antiviral agent present is the ordinary dosage required to obtain the desired result. Such dosages are known to the skilled practitioner in the medical arts and are not a part of the present invention. In a preferred embodiment, the antiviral agent in the therpeutic composition is present in an amount from about 0.1% to about 20%, preferably from about 1% to about 10%, and more preferably from about 2% to about 7%, by weight.

The antifungal agents which may be employed in the therapeutic compositions may be selected from a wide variety of water-soluble and water-insoluble drugs, and their acid addition or metallic salts, useful for treating pulmonary diseases. Both organic and inorganic salts may be used provided the antifungal agent maintains its medicament value. The antifungal agents may be selected from a wide range of therapeutic agents and mixtures of therapeutic agents which may be administered in sustained release or prolonged action form. Nonlimiting illustrative specific examples of antifungal agents include the following medicaments: miconazole, clotrimazole, tioconazole, terconazole, povidone-iodine, and butoconazole. Other antifungal agents are lactic acid and sorbic acid. Preferred antifungal agents are miconazole and clotrimazole.

The amount of antifungal agent which may be employed in the therapeutic compositions of the present invention may vary depending upon the therapeutic dosage recommended or permitted for the particular antifungal agent. In general, the amount of antifungal agent present is the ordinary dosage required to obtain the desired result. Such dosages are known to the skilled practitioner in the medical arts and are not a part of the present invention. In a preferred embodiment, the antifungal agent in the therapeutic composition is present in an amount from about 0.05% to about 10%, preferably from about 0.1% to about 5%, and more preferably from about 0.2% to about 4%, by weight.

The antitumor agents which may be employed in the therapeutic compositions may be selected from a wide variety of water-soluble and water-insoluble drugs, and their acid addition or metallic salts, useful for treating pulmonary diseases. Both organic and inorganic salts may be used provided the antitumor agent maintains its medicament value. The antitumor agents may be selected from a wide range of therapeutic agents and mixtures of therapeutic agents which may be administered in sustained release or prolonged action form. Nonlimiting illustrative specific examples include anti-metabolites, antibiotics, plant products, hormones, and other miscellaneous chemotherapeutic agents. Chemically reactive drugs having nonspecific action include alkylating agents and N-alkyl-N-nitroso compounds. Examples of alkylating agents include nitrogen mustards, azridines (ethylenimines), sulfonic acid esters, and epoxides. Anti-metabolites are compounds that interfere with the formation or utilization of a normal cellular metabolite and include amino acid antagonists, vitamin and coenzyme antagonists, and antagonists of metabolites involved in nucleic acid synthesis such as glutamine antagonists, folic acid antagonists, pyrimidine antagonists, and purine antagonists. Antibiotics are compounds produced by microorganisms that have the ability to inhibit the growth of other organisms and include actinomycins and related antibiotics, glutarimide antibiotics, sarkomycin, fumagillin, streptonigrin, tenuazonic acid, actinogan, peptinogan, and anthracyclic antibiotics such as doxorubicin. Plant products include colchicine, podophyllotoxin, and vinca alkaloids. Hormones include those steroids used in breast and prostate cancer and corticosteroids used in leukemias and lymphomas. Other miscellaneous chemotherapeutic agents include urethan, hydroxyurea, and related compounds; thiosemicarbazones and related compounds; phthalanilide and related compounds; and triazenes and hydrazines. The the anticancer agent may also be a monoclonal antibody or the use of X-rays. In a preferred embodiment, the anticancer agent is an antibiotic. In a more preferred embodiment, the anticancer agent is doxorubicin. In a most preferred embodiment, the anticancer agent is doxorubicin.

The amount of antitumor agent which may be employed in the therapeutic compositions of the present invention may vary depending upon the therapeutic dosage recommended or permitted for the particular antitumor agent. In general, the amount of antitumor agent present is the ordinary dosage required to obtain the desired result. Such dosages are known to the skilled practitioner in the medical arts and are not a part of the present invention. In a preferred embodiment, the antitumor agent in the therapeutic composition is present in an amount from about 1% to about 50%, preferably from about 10% to about 30%, and more preferably from about 20% to about 25%, by weight.

Nitric oxide is preferably employed as a gas that is nebulized to assure that proper amounts are delivered. Nitric oxide may be placed in an inert formula. The preferred route of administration is by inhalation. In a preferred embodiment, a sterile solution of nitric oxide mediator and/or nitric oxide source is nebulized and inhaled by the patient. A therapeutically effective amount of nitric oxide mediator and/or nitric oxide source is inhaled. This may be accomplished in a single inhalation or by repeated inhalations over a period of time typically 1 to 30 minutes. Preferably, inhalation will be complete in less than 20 minutes. Most preferably inhalation will be complete in less than 15 minutes. Patients with adult respiratory distress syndrome are generally given nitric oxide for 30 minutes at 20 ppm. Patients with adult respiratory distress syndrome may also be given nitric oxide for 7 hours or several days at 2 ppm in a tent or with a mask.

Pyruvate controls the positive and negative effects of nitric oxide at higher levels. Too high a level of nitric oxide is detrimental to cells. Pyruvate will protect cells from excess nitric oxide and this explains its effect on mild asthmatics. Moderate to severe asthmatics and emphysema patients produce much higher levels of oxygen radicals especially in smokers, and it would be expected that higher levels of pyruvate would produce better results in these patients. The ability to control the levels of nitric oxide is important. Over production or under production is detrimental and produces various diseases in both the lungs and nasal cavities. Pyruvate, at 0.5 mM levels, protects nitric oxide and can be used in diseases where nitric oxide production is low, i.e. in smokers (21), mild asthmatics (21), in intubated or tracheostomized patients (19), in normal subjects after exercise and hyperventilation (21), COPD patients (22), and in patients with cystic fibrosis (22). In asthmatics, exhaled nitric oxide levels are significantly elevated prior to an attack, then the exhaled nitric oxide levels are significantly reduced by 20–40% immediately after a 20% fall in FEV1 by histamine, AMP, or hypertonic saline challenge in steroid naive asthmatic subjects (21). Patients who produce excess nitric oxide include those with kartagener's syndrome (22), moderate or severe asthma (22), sarcoidosis (22), and fibrosing alveolitis (22). Increased nitric oxide levels are chemotactic for eosinophils, which produce and enhance inflammation (20). Eosinophils affects dyspnoea perception in asthma by releasing neurotoxins (20). Inhaled B2 agonists do not have any effect on nitric oxide production and this presumably affects their lack of effect on chronic inflammation in asthma (23). Acute treatment with corticosteriods during an exacerbation of asthma is associated with a decline in nitric oxide values in adults and children (23). Nitric oxide is elevated in the nasal cavities of healthy newborns and in healthy adults (24). Nitric oxide is markedly reduced in the nasal cavities of children suffering from cystic fibrosis, and in patients with chronic sinusitis (24), allergic rhinitis (25), with respiratory disorders (25) and pre-eclampsia (25). When inhaled, nasally derived nitric oxide reaches the lower airways and the lungs, and nitric oxide may be involved in the regulation of pulmonary functions and primary host defenses (25).

Excess sodium pyruvate beyond that needed to neutralize oxygen radicals will enter the bronchial and lung cells. All cells have a transport system that allow cells to concentrate pyruvate at higher concentrations than serum levels. In the cell, pyruvate raises the pH level, increases levels of ATP, decreasing levels of ADP and cAMP, and increases levels of GTP, while decreasing levels of cGMP. Nitric oxide acts in the opposite mode by increasing levels of cGMP and ADP, and requires an acid pH range in which to work. Generally, the body will make normal levels of pyruvate but will produce higher levels in response to $NO_2$ which is produced from nitric oxide and $H_2O_2$.

In summary, pyruvate enhances nitric oxide availability to effect bronchodilation by protecting it from oxygen radicals, enhancing its synthesis, and by regulating its effect intracellularly and thus maintaining appropriate cellular levels and functions for nitric oxide. It is believed that nitric oxide is therapeutically effective in patients with adult respiratory distress syndrome and in patients with persistent pulmonary hypertension of neonates because both diseases produce severe hypoxemia (reduction of oxygen, deficient oxygenation), which inhibits the production of oxygen radicals that can react with nitric oxide to produce $NO_2$, which is known to induce acute lung injury. In patients with COPD, nitric oxide treatment has not produced efficacious results because most COPD patients produce oxygen radicals that react with nitric oxide to produce $NO_2$. Combining the inhalation of nitric oxide with pyruvate would produce the desired effect, enhancing the efficacy of an approved drug. This combination can be used in the lungs or in the nasal cavities where low production of nitric oxide is found. Nitric oxide is also a natural antimicrobial agent used to kill invading microorganisms. The combination of pyruvate and nitric oxide would be effective for the treatment of tumors, bacterial infections, fungal infections, viral infections, angina, ischemic diseases, and congestive heart failure. In diseases where overproduction of nitric oxide is detrimental, excess pyruvate can be used alone to lower nitric oxide synthesis. Excess pyruvate is sufficient pyruvate to neutralize $H_2O_2$ and to enter the cell to counter the effects of nitric oxide. Excess pyruvate acts in the opposite direction of nitric oxide.

The term "injured cell" as used herein means a cell which has some or all of the following: (a) injured membranes so that transport through the membranes is diminished and may result in one or more of the following, an increase in toxins and normal cellular wastes inside the cell and/or a decrease in nutrients and other components necessary for cellular repair inside the cell, (b) an increase in concentration of oxygen radicals inside the cell because of the decreased ability of the cell to produce antioxidants and enzymes, and (c) damaged DNA, RNA and ribosomes which must be repaired or replaced before normal cellular functions can be resumed.

The carrier composition is selected from the group consisting of tablets, capsules, liquids, isotonic liquids, isotonic media, enteric tablets and capsules, parenterals, topicals, creams, gels, ointments, chewing gums, confections and the like.

Obviously, numerous modifications and variations of the present invention are possible in the light of the above teachings and the invention is not limited to the example herein. It is therefore understood that within the scope of the appended claims, the invention may be practiced otherwise than as specifically described herein.

Throughout this application, various publications have been referenced. The disclosures in these publications are incorporated herein by reference in order to more fully describe the state of the art.

REFERENCES

1. Hardman, J. et al., The pharmacological basis of therapeutics. Ninth edition 1996, pp. 137–356.

2. Moncada, S. et al, Nitric Oxide: physiology, pathophysiology, and pharmacology. 1991 Pharmacological Reviews Vol. 43 no pp 109–141.

3. Nathan, C., Nitric oxide as a secretory product of mammalian cells. FASEB journal vol. Sep. 6, 1992 pp 3051–3064.

4. Rossaint, R. et al, Inhaled nitric oxide: its effect on pulmonary circulation and airway smooth muscle cells. Euro Heart Jour. 1993 vol. 14 Supp. pp 133–140.

5. Mattes, K. et al. NO in exhaled air is correlated with markers of eosinophilic airway inflammation in corticosteroid-dependent childhood asthma. Euro Respir J. 1999 vol. 13, pp 1391–1395

6. Artlich, A. et al., Childhood asthma: exhaled nitric oxide in relation to clinical symptoms. Euro Respir. J. Vol. 13, pp 1395–1401.

7. Jobsis, Q. et al. Sampling of exhaled nitric oxide in children: end expiratory plateau, balloon and tidal breathing methods compared. Euro Respir. J. Vol. 13, pp 1406–1410.

8. Mukala, K. et al. Personally measured weekly exposure to $NO_2$ and respiratory health among preschool children. Euro. Respir. J. Vol. 13, pp 1411–1417.

9. Stanko R., The power of Pyruvate 1999, Keats Publishing.

10. Kelly, F. et al. Antioxidant kinetics in lung ravage fluid following exposure of humans to nitrogen dioxide. Am. J. Respir. Crit Med. Vol. 154 1991 pp 1700–1705.

11. Roberts, J. et al. Inhaled nitric oxide and persistent pulmonary hypertension of the new borns. The new England Journal of Medicine Feb. 27, 1997 pp 605–610.

12. Lehninger 1981 Biochemistry, Worths Publishing.

13. Comhair, S. et al. Rapid loss of superoxide dismutase activity during antigen-induced asthmatic response. Lancet vol. 355 Feb. 19 2000.

14. Stewart R M, et al., Hydrogen peroxide contracts airway smooth muscle: a possible endogenous mechanism. Respir. Physiol 1981 45: 333–342.

15. Rhoden K J, Barnes P J: Effect of hydrogen peroxide on guinea pig tracheal smooth muscle in vitro: role of cyclo-oxygenase and airway epithelium. Br. J Pharmacol 1989 98: 325–330

16. Motojima S, et al. Toxicity of eosinophil cationic proteins for guinea pig tracheal epithelium in vitro. Am Rev Respir Dis 1989 139: 801–805

17. Sporn P H, et al. Hydrogen peroxide induced arachidonic acid metabolism in rat alveolar macrophage. Am Rev Respir Dis 1988 137: 49–56

18. Postma, D. S. et al Association between nonspecific bronchial hyperreactivity and superoxide anion production by polymorphonuclear leukocytes in chronic air flow obstruction. Am. Rev Respirdis. (1988) 137: 57–61.

19. Alving, K. Methodological aspects of exhaled nitric oxide measurements Euro Respir Rev 1999: 9:68, 208–211

20. Kharitonov, S. Exhaled nitric oxide and carbon monoxide in asthma. Euro Respir. Rev. 1999, 9:68, 212–216.

21. Gouw, P. et al. Stimuli affecting exhaled nitric oxide in asthma. Euro Respir. Rev. 1999; 9:68, 219–222.

22. Kharitonov, S. Exhaled nitric oxide and carbon monoxide in respiratory diseases. Euro Respir. Rev. 1999; 9:68, 223–226.

23. Barnes, P. The effect of drugs on exhaled nitric oxide. Euro Respir. Rev. 1999; 9:68, 231–233.

24. Baraldi, E. et al. Application of exhaled nitric oxide measurement in pediatrics. Euro Respir. Rev. 1999; 9:68, 234–240.

25. Lundberg, J. Nitric oxide in the nasal airways. Euro Respir. Rev. 1999; 9:68, 241–245

26. Culpitt, S. The measurement of hydrogen peroxide in airways disease. Euro Respir. Rev. 1999; 9:68, 246–248.

27. Montuschi, P. Isoprostanes and other exhaled markers in respiratory diseases. . Euro Respir. Rev. 1999; 9:68, 249–253.

28. Robertson, F M, Gene expression and cellular sources of inducible nitric oxide synthase during tumor promotion. Carcinogenesis September; 1996 17 (9): 2053–9.

29. Soler M N, et al, Gene therapy of rat medullary thyroid cancer by naked nitric oxide synthase II DNA injection. J Gene Med September–October; 2000 2(5): 433–52.

30. Wang H H, B 16 melanoma cell arrests in mouse liver induces nitric oxide release and sinusoidal cytotoxicity: a natural hepatic defense against metastasis. Cancer Res Oct. 15, 2000 60(20): 5862–9.

31. Brennan P A., The action and interactions of nitric oxide in solid tumors. Eur J Surg Oncol Aug. 26, 2000 (5): 434–7.

32. Rieder J, et al. Different patterns of inducible nitric oxide synthase gene expression in ovarian carcinoma cell lines. Anticancer Res September–October; 2000 20(5A): 3251–8.

While the method for treating the disease state in mammalian cells involved in the inflammatory response herein described constitute preferred embodiments of this invention, it is to be understood that the invention is not limited to this precise form of method and that changes may be made therein without departing from the scope of the invention which is defined in the appended claims.

I claim:

1. A method for treating a pulmonary disease state in mammals by altering indigenous in vivo levels of nitric oxide in mammalian cells comprising contacting the mammalian cells with a therapeutically effective amount of a nitric oxide mediator, wherein the nitric oxide mediator is selected from the group consisting of pyruvates, pyruvate precursors, α-keto acids having four or more carbon atoms, precursors of α-keto acids having four or more carbon atoms, and the salts thereof.

2. The method according to claim 1, wherein the pyruvates are selected from the group consisting of pyruvic acid, lithium pyruvate, sodium pyruvate, potassium pyruvate, magnesium pyruvate, calcium pyruvate, zinc pyruvate, manganese pyruvate, and mixtures thereof.

3. The method according to claim 1, wherein the pyruvate precursors are selected from the group consisting of pyruvyl-glycine, pyruvyl-alanine, pyruvyl-leucine, pyruvyl-valine, pyruvyl-isoleucine, pyruvyl-phenylalanine, pyruvamide, salts of pyruvic acid, and mixtures thereof.

4. The method according to claim 1, wherein the α-keto acids having four or more carbon atoms are selected from the group consisting of oxaloacetic acid, keto-glutaric acid, keto-butyric acid, keto-adipic acid, keto-caproic acid, keto-isovaleric acid, their salts and mixtures thereof.

5. The method according to claim 1, wherein the precursors of α-keto acids having four or more carbon atoms are selected from the group consisting of α-keto acid-glycine, α-keto acid-cystine, α-keto acid-alanine, α-keto acid-leucine, α-keto acid-valine, α-keto acid-isoleucine, α-keto acid-phenylalanine, α-keto amide, their salts and mixtures thereof.

6. The method according to claim 1, wherein the disease state is selected from the group consisting of bacterial infections, fungal infections, viral infections, and tumors.

7. The method according to claim 6, wherein the disease state is a tumor selected from the group consisting of epidermoid carcinomas, small cell carcinomas, adenocarcinomas, and large cell carcinomas.

8. The method according to claim 6, wherein the disease state is selected from the group consisting of bacterial infections, fungal infections, and viral infections.

9. The method according to claim 1, wherein the levels of nitric oxide in the mammalian cells are abnormally low in the disease state.

10. The method according to claim 1, wherein the levels of nitric oxide in the mammalian cells are abnormally high in the disease state.

11. The method according to claim 1, wherein the nitric oxide mediator is present in an amount from about 0.1 millimoles to about 5 millimoles.

12. The method according to claim 11, wherein the nitric oxide mediator is present in an amount from about 0.2 millimoles to about 4.0 millimoles.

13. The method according to claim 1, further comprising contacting the mammalian cells with a nitric oxide source selected from the group consisting of nitric oxide, nitric oxide precursors, and nitric oxide stimulators.

14. The method according to claim 13, wherein the nitric oxide source is nitric oxide.

15. The method according to claim 13, wherein the nitric oxide precursor or nitric oxide stimulator is selected from the group consisting of L-arginine, ADP, and arachidonic acid.

16. The method according to claim 13, wherein the disease state is selected from the group consisting of bronchial asthma, acute bronchitis, emphysema, chronic obstructive emphysema, centrilobular emphysema, panacinar emphysema, chronic obstructive bronchitis, reactive airway disease, cystic fibrosis, bronchiectasis, acquired bronchiectasis, kartaagener's syndrone, acelectasis, acute atelectasis, chronic acelectasis, pneumonia, essential thrombocytemia, legionnaire's disease, psittacosis, fibrogenic dust disease, diseases due to organic dust, diseases due to irritant gases and chemicals, hypersensitivity diseases of the lung, idiopathic infiltrative diseases of the lungs, chronic obstructive pulmonary disorder, and adult respiratory distress syndrome.

17. The method according to claim 16, wherein the disease state is emphysema or asthma.

18. The method according to claim 13, wherein the nitric oxide source is present in an amount from about 10 ppm to about 50 ppm.

19. The method according to claim 18, wherein the nitric oxide source is present in an amount from about 15 ppm to about 45 ppm.

20. The method according to claim 13, wherein the nitric oxide mediator is administered prior to administration of the nitric oxide source.

21. The method according to claim 13, wherein the nitric oxide mediator is administered concomitantly with administration of the nitric oxide source.

22. The method according to claim 13, wherein the nitric oxide mediator is administered after administration of the nitric oxide mediator.

23. The method according to claim 1, further comprising contacting the mammalian cells with a therapeutic agent.

24. The method according to claim 23, wherein the therapeutic agent is selected from the group consisting of antibacterials, antivirals, antifungals, antitumors, antihistamines, proteins, enzymes, hormones, nonsteroidal anti-inflammatories, cytokines, and steroids.

25. The method according to claim 23, wherein the therapeutic agent is administered prior to administration of the nitric oxide mediator.

26. The method according to claim 23, wherein the therapeutic agent is administered concomitantly with administration of the nitric oxide mediator.

27. The method according to claim 23, wherein the therapeutic agent is administered after administration of the nitric oxide mediator.

28. The method according to claim 1, further comprising contacting the mammalian cells with a therapeutic agent and a nitric oxide source selected from the group consisting of nitric oxide, nitric oxide precursors, and nitric oxide stimulators.

29. The method according to claim 1, wherein the nitric oxide mediator is inhaled.

* * * * *

UNITED STATES PATENT AND TRADEMARK OFFICE
CERTIFICATE OF CORRECTION

PATENT NO.         : 6,689,810 B2
APPLICATION NO.    : 10/205353
DATED              : February 10, 2004
INVENTOR(S)        : Alain Martin Page 1 of 1

It is certified that error appears in the above-identified patent and that said Letters Patent is hereby corrected as shown below:

In claim 11 at column 17, line 57 - line 58 kindly correct "from about 0.1 millimoles to about 5 millimoles." to "from about 0.0001 millimoles to about 0.025 millimoles."

In claim 12 at column 17, line 60 - line 61 kindly correct "from about 0.2 millimoles to about 4.0 millimoles." to "from about 0.0002 millimoles to about 0.020 millimoles."

Signed and Sealed this
Sixth Day of December, 2011

David J. Kappos
*Director of the United States Patent and Trademark Office*